(12) United States Patent
Wang et al.

(10) Patent No.: US 12,049,657 B1
(45) Date of Patent: Jul. 30, 2024

(54) TYPE III COLLAGEN PEPTIDE AND PREPARATION METHOD THEREOF

(71) Applicant: Beijing Qingyan Boshi Health Management Co., Ltd., Beijing (CN)

(72) Inventors: Haiyan Wang, Beijing (CN); Jingqi Liu, Beijing (CN); Aiqing Liu, Beijing (CN)

(73) Assignee: BEIJING QINGYAN BOSHI HEALTH MANAGEMENT CO., LTD., Beijing (CN)

( * ) Notice: Subject to any disclaimer, the term of this patent is extended or adjusted under 35 U.S.C. 154(b) by 0 days.

(21) Appl. No.: 18/544,368

(22) Filed: Dec. 18, 2023

(30) Foreign Application Priority Data

Apr. 27, 2023 (CN) .......................... 202310465757.7

(51) Int. Cl.
*C12P 21/06* (2006.01)
*C07K 14/78* (2006.01)

(52) U.S. Cl.
CPC .............. *C12P 21/06* (2013.01); *C07K 14/78* (2013.01)

(58) Field of Classification Search
CPC .................................. C12P 21/06; C07K 14/78
See application file for complete search history.

(56) References Cited

FOREIGN PATENT DOCUMENTS

| CN | 1802437 A | 7/2006 |
|---|---|---|
| CN | 114634549 A | 6/2022 |
| CN | 115717148 A | 2/2023 |

OTHER PUBLICATIONS

Zengliu Song et al., Characterization and comparison of collagen extracted from the skin of the Nile tilapia by fermentation and chemical pretreatment, Food Chemistry, Sep. 25, 2020, pp. 1-8, vol. 340 (2021), Issue No. 128139.

*Primary Examiner* — Suzanne M Noakes
(74) *Attorney, Agent, or Firm* — Zhigang Ma

(57) ABSTRACT

A type III collagen peptide and a preparation method thereof are provided. The preparation method includes: degreasing a raw material, performing ultrasonic treatment and fermentation to obtain a total crude protein extract; extracting a crude collagen extract under an acidic condition; adding a clarificant to remove impurities; adding *Bacillus coagulans* for fermentation to obtain a type III collagen; adding a compound protease for enzymolysis, followed by inoculating *staphylococcus simulans* for fermentation; and separating and purifying to obtain the type III collagen peptide. The type III collagen peptide has an average molecular weight of 300-3,000 Daltons, contains a symbolic peptide fragment of type III collagen, is safe, free of toxic and side effects, and easy to digest, can be used as a raw material of medicines, cosmetics, dietary supplements, and food, and be added into acidic beverages, and can promote generation of type III collagen in human's body.

12 Claims, No Drawings

TYPE III COLLAGEN PEPTIDE AND PREPARATION METHOD THEREOF

TECHNICAL FIELD

The disclosure relates to the technical field of polypeptide preparation, particularly to a type III collagen peptide and a preparation method thereof.

BACKGROUND

Collagen peptide is a peptide product in small molecules degraded from a collagen in large molecules by means of protease, and the collagen peptide is easily digested and absorbed. The collagen peptide can promote bone formation and enhance a bone collagen structure at a low calcium level, thereby improving bone strength and preventing osteoporosis. Moreover, the collagen peptide can also protect gastric mucosa, resist ulcer, and resist allergy; particularly, the collagen peptide has excellent beauty effects, and is capable of improving skin moisture, reducing wrinkles, resisting aging, etc.; therefore, the collagen peptide is widely used in the fields of food, medicine, tissue engineering, cosmetics, etc., and is also accepted by vast consumers as a basic raw material in oral beauty products.

There are more than 20 types of collagen; however, at present, there are many studies on type I collagen peptide and type II collagen peptide, and the type I and II collagen peptides have been industrialized for production. For example, Wang Lin's presentation of "*Studies on the preparation, identification of CP I and its protective effect on cells damaged by UVA*" compares three crude extraction methods, i.e., acid dissolution method, enzymatic hydrolysis method, and neutral salt solution method, by using hogskin as a raw material. It is found that the enzymatic hydrolysis method has the highest crude extraction yield, and combined with high-performance liquid chromatography for separation and purification, can obtain a type I collagen; and the above-mentioned method has high efficiency and selectivity, and the obtained type I collagen can effectively prevent the damage caused by UVA oxidation. Chinese patent publication No. CN114085285A discloses a preparation method and an application of a high-purity type II collagen peptide with bone joint maintenance effect, which obtains the high-purity type II collagen peptide by steps of removing impurities from cartilage, cleaning bone grains, carrying out bone grain enzymolysis, carrying out multi-stage filtration, carrying out nanofiltration, impurity removal and concentration, carrying out resin refining and impurity removal, sterilizing, carrying out concentration, and carrying out spray drying; and the above-mentioned method can greatly improve the content of type II collagen peptide and achieve preparation of collagen granular powder with good instant solubility.

However, the preparation of the type III collagen peptide mainly focuses on a recombinant expression of collagen, which refers to the amino acid sequences or fragments encoded by specific genes designed and modified by gene recombination technology, or combinations of amino acid sequence fragments with specific functions. However, there is relatively little research on extracting the type III collagen from animal tissues.

Chinese patent publication No. CN101717804A discloses a method for preparing a medical type III collagen, specially including: pre-treating fresh newborn kip as a raw material and then extracting a mixture of type I and type III collagens by using a pepsin degradation limiting method and a salting out method; dissolving the mixture with Tris-sodium chloride (NaCl) buffer solution to remove most of the type I collagen, and denaturating the collagen with the Tris-HCl buffer solution to obtain the type III collagen.

Although certain progress has been achieved for the development and research of type III collagen peptide, severe problems such as high difficulty, low purity, high cost, etc., still exist in extracting the type III collagen from animal tissues. Therefore, it is essential to develop a method for preparing a type III collagen peptide.

SUMMARY

In view of the above, objectives of the disclosure are to make up for the deficiencies in the related art, and to provide a type III collagen peptide and a preparation method thereof. The obtained type III collagen peptide contains a symbolic peptide fragment of a type III collagen, an average molecular weight thereof is in a range of 300-3,000 daltons (abbreviated as Dal, Da, or D), and is capable of improving skin moisture, promoting the generation of type III collagen in human's body, and playing a role in delaying tissue aging.

In order to achieve the above objectives, the disclosure adopts the following technical solution.

In a first aspect, the preparation method of the type III collagen peptide includes the following steps:
- step 1, degreasing a raw material to obtain a degreased raw material, performing ultrasonic treatment and fermentation on the degreased raw material to obtain a total crude protein extract;
- step 2, extracting a crude collagen extract from the total crude protein extract under an acidic condition;
- step 3, adding a clarificant to remove impurities in the crude collagen extract;
- step 4, adding *Bacillus coagulans* for fermentation to obtain a type III collagen;
- step 5, adding a compound protease to the type III collagen for enzymolysis, followed by inoculating *Staphylococcus simulans* for fermentation to obtain enzymatic fermentation solution; and
- step 6, separating and purifying the enzymatic fermentation solution to obtain the type III collagen peptide.

By adopting the above-mentioned method according to the disclosure, production conditions of extracting the type III collagen peptide from animal tissues are optimized. Specially, the type III collagen peptide prepared through mutual coordination and combined action of processes of *Bacillus coagulans* fermentation, compound protease enzymolysis, and *Staphylococcus simulans* fermentation, contains the symbolic peptide fragment of type III collagen, and has an average molecular weight in a range of 300-3,000 D. Moreover, the prepared type III collagen peptide is safe, free of toxic and side effects, and is easy to digest, thereby being used as a raw material of medicines, cosmetics, dietary supplements, and food, and being added into acidic beverages. Furthermore, the prepared type III collagen peptide can be used for improving skin moisture and promoting the generation of type III collagen in human's body.

In an embodiment, the step 1 further includes the following steps:
- immersing the raw material in sodium hydroxide (NaOH) solution, taking out and washing the raw material to be neutral, then mixing the raw material with water according to a mass ratio of the raw material to the water of 1: 5-40, performing the ultrasonic treatment for 1-3 times, taking out the raw material after performing the ultrasonic treatment, then adding the raw material into water with a 1-10 times volume of the raw material again to obtain feed liquid, and inoculating *Cladosporium* and/or *Candida famata* for the fermentation according to a weight of the feed liquid, thereby obtaining the total crude protein extract.

In an embodiment, in the step 1, the raw material is one selected from the group consisting of an animal skin, an animal scale, and an animal bone. Specially, the raw material is one selected from the group consisting of a tilapia, a cod, a sheepskin, a cowhide, and a poultry skin.

In an embodiment, in the step 1, a mass fraction of the NaOH solution is in a range of 0.1%-5%, and a time for the immersing is in a range of 4-18 hours (h).

In an embodiment, in the step 1, a power for the ultrasonic treatment is in a range of 150-400 watts (W), a wind speed of the ultrasonic treatment is in a range of 5-500 meter per second (m/s), a time for the ultrasonic treatment is in a range of 10-80 minutes (min), and a number of times of the ultrasonic treatment is in a range of 1-3 times.

In an embodiment, in the step 1, an inoculation amount of the *Cladosporium* is in a range of $1-8\times10^5$ colony-forming units per gram (CFU/g), and an inoculation amount of the *Candida famata* is in a range of $1-8\times10^5$ CFU/g.

In an embodiment, in the step 1, a temperature for the fermentation is in a range of 25 degrees Celsius (° C.) to 35° C., and a time for the fermentation is in a range of 2-10 h.

In an embodiment, the step 2 further includes the following steps:
adding the total crude protein extract to purified water with a 2-50 times mass of the total crude protein extract, adjusting a potential of hydrogen (pH) value of the total crude protein extract to a range of 2-5, heating the total crude protein extract added with the purified water to a temperature of 50° C.-90° C., and preserving the temperature and extracting the total crude protein extract for 2-8 h to prepare the crude collagen extract.

In an embodiment, the step 3 further includes the following steps:
adjusting a pH value of the crude collagen extract to a range of 2-7, adding the clarificant to the crude collagen extract, stewing the crude collagen extract added with the clarificant for 2-8 h to remove the impurities, and then obtaining a supernatant for later use.

In an embodiment, in the step 3, the clarificant is a mixture of soybean polysaccharide, egg white, and potato starch; and a mixing mass ratio of the soybean polysaccharide:the egg white:the potato starch is in a range of 1:2-4:1-3; and an addition amount of the clarificant is in a range of 0.5%-3% of a mass of the crude collagen extract.

In an embodiment, the step 4 further includes the following steps:
adding the *Bacillus coagulans* to the supernatant obtained in the step 3, adjusting a pH value of the supernatant added with the *Bacillus coagulans* to a range of 6-7.5, and performing the fermentation on the supernatant added with the *Bacillus coagulans* at 40° C.-55° C. for 2-6 h to obtain the type III collagen.

In an embodiment, in the step 4, an addition amount of the *Bacillus coagulans* is in a range of 0.1%-1% of a mass of the supernatant.

In an embodiment, the step 5 further includes the following steps:
adjusting a pH value of the type III collagen to a range of 7.5-8.0, adding the compound protease to the type III collagen to perform the enzymolysis to obtain an enzymatic hydrolysate; adjusting a pH value of the enzymatic hydrolysate to a range of 6-7.5, and then inoculating the *Staphylococcus simulans* according to a weight of the enzymatic hydrolysate to perform the fermentation on the enzymatic hydrolysate added with the *Staphylococcus simulans*, thereby obtaining the enzymatic fermentation solution.

In an embodiment, in the step 5, the compound protease includes: an alkaline protease and a self-made protease, and the self-made protease includes: a ginger protease (also referred to as a self-made ginger protease) and a squid viscera protease (also referred to as a self-made squid viscera protease); a mass ratio of the alkaline protease:the ginger protease:the squid viscera protease is in a range of 2.5-4:0.8-1.5:1, especially for 3:1:1; and an addition amount of the compound protease is in a range of 0.5%-2% of a mass of the type III collagen, a temperature for the enzymolysis is in a range of 50° C.-60° C., and a time for the enzymolysis is in a range of 2-8 h.

In an embodiment, in the step 5, the *Staphylococcus simulans* is self-separated from Hunan bacon and is identified by phenotype and biochemical identification; and an inoculation amount of the *Staphylococcus simulans* is in a range of $1-9\times10^8$ CFU/g; a temperature for the fermentation is in a range of 35° C.-40° C.; and a time for the fermentation is in a range of 2-6 h.

In an embodiment, in the step 6, steps of the separating and purifying include ultrafiltration, nanofiltration, and spray drying.

In an embodiment, in the step 6, a molecular weight-cut-off of an ultrafiltration membrane used in the ultrafiltration is in a range of 1-10 kilodaltons (kD), and the ultrafiltration membrane is a polysulfone or a polyamide spiral-wound membrane.

In an embodiment, in the step 6, a molecular weight-cut-off of a nanofiltration membrane used in the nanofiltration is in a range of 100-2,000 D, and the nanofiltration membrane is one selected from the group consisting of a polyamide, a sulfonated polyethersulfone, and a sulfonated polysulfone hollow fiber membrane.

In an embodiment, in the step 6, an inlet temperature of the spray drying is set to be in a range of 160° C.-220° C.; and an outlet temperature of the spray drying is set to be in a range of 90° C.-120° C.

According to the disclosure, membrane filtration is used to perform the separating and purifying, and the ultrafiltration and the nanofiltration are used to remove inorganic salts and water-soluble free amino acids, all of which are performed at room temperature, have no phase changes, are efficient and energy-saving, do not affect the activity of small molecule peptide, and do not produce pollution during the production process.

In a second aspect, the type III collagen peptide obtained in the preparation method according to the first aspect has the average molecular weight in the range of 300-3,000 D, and contains the symbolic peptide fragment of the type III collagen.

Compared with the related art, the disclosure has beneficial effects as follows.

The disclosure provides the preparation method of the type III collagen peptide, the average molecular weight of which is 300-3,000 D by means of the mutual coordination and combined action of processes of *Bacillus coagulans* fermentation, compound protease enzymolysis, and *Staphylococcus simulans* fermentation. Moreover, the obtained type III collagen peptide is safe, free of toxic and side effects, and is easy to digest, thereby being used as a raw material of medicines, cosmetics, dietary supplements, and food, and being added into acidic beverages. Furthermore, the obtained type III collagen peptide can be used for improving skin moisture, promoting the generation of type III collagen in human's body, and playing a role in delaying tissue aging.

DETAILED DESCRIPTION OF EMBODIMENTS

The following non-limiting embodiments may enable those skilled in the related art to more fully understand the disclosure, but are not intended to limit the disclosure in any way. The following is merely an exemplary description of the scope of the protection of the disclosure, and those skilled in the related art may make various changes and modifications to the disclosure according to the disclosed content, which should also fall within the scope of the protection of the disclosure.

In an illustrated embodiment of the disclosure, a preparation method of a type III collagen peptide is provided, including the following steps:

step 1, immersing a raw material in sodium hydroxide (NaOH) solution with a mass fraction of 0.1%0-5%% for 4-18 hours (h), and then washing the raw material to be neutral, then mixing the raw material with water according to a mass ratio of the raw material to the water of 1: 5-40, performing ultrasonic treatment for 1-3 times at a power of 150-400 watts (W) and a wind speed of 5-500 meter per second (m/s), each time of the ultrasonic treatment being performed for 10-80 minutes (min); taking out the raw material after performing the ultrasonic treatment, then adding the raw material into water with a 1-10 times volume of the raw material again to obtain feed liquid, and inoculating *Cladosporium* and/or *Candida famata* for a fermentation according to a weight of the feed liquid, an inoculation amount of the *Cladosporium* being in a range of $1-8\times10^5$ colony-forming units per gram (CFU/g), and an inoculation amount of the *Candida famata* being in a range of $1-8\times10^5$ CFU/g, and performing the fermentation at 25 degrees Celsius (C) to 35° C. for 2-10 h, thereby obtaining a total crude protein extract;

step 2, adding the total crude protein extract to purified water with a 2-50 times mass of the total crude protein extract to obtain a mixed solution, adding a potential of hydrogen (pH) regulator (NaOH and/or hydrochloric acid (HCl) solution, a mass fraction of the pH regulator being 5%-30%) to the mixed solution to adjust a pH value of the crude collagen extract to a range of 2-5, heating the total crude protein extract added with the purified water to a temperature of 50° C.-90° C., and preserving the temperature and extracting the total crude protein extract for 2-8 h to prepare a crude collagen extract;

step 3, adjusting a pH value of the crude collagen extract to a range of 2-7, mixing 1 g of soybean polysaccharide, egg white, and potato starch according to a mass ratio of the soybean polysaccharide:the egg white:the potato starch being in a range of 1: 2-4:1-3 to prepare a clarificant, and then adding the clarificant to the crude collagen extract, an addition amount of the clarificant being in a range of 0.5%-3% of a mass of the crude collagen extract, stewing the crude collagen extract added with the clarificant for 2-8 h to remove impurities, and then obtaining a supernatant for later use;

step 4, adding *Bacillus coagulans* in a range of 0.1%-1% of a mass of the supernatant into the supernatant, adjusting a pH value of the supernatant added with the *Bacillus coagulans* to a range of 6-7.5, and performing a fermentation on the supernatant added with the *Bacillus coagulans* at 40° C.-55° C. for 2-6 h to obtain a type III collagen;

step 5, adjusting a pH value of the type III collagen to a range of 7.5-8.0, adding a compound protease in a range of 0.5%-2% of a mass of the type III collagen (the compound protease including an alkaline protease and a self-made protease, the self-made protease including a ginger protease and a squid viscera protease, a mass ratio of the alkaline protease:the ginger protease:the squid viscera protease being in a range of 2.5-4:0.8-1.5:1, preferably 3:1:1) to the type III collagen to perform an enzymolysis at 50° C.-60° C. for 2-8 h to obtain an enzymatic hydrolysate; adjusting a pH value of the enzymatic hydrolysate to a range of 6-7.5 by using a hydrochloric acid solution and a sodium hydroxide solution, and then inoculating a range of $1-9\times10^8$ CFU/g of *Staphylococcus simulans* according to a weight of the enzymatic hydrolysate to perform a fermentation on the enzymatic hydrolysate added with the *Staphylococcus simulans* at 35° C.-40° C. for 2-6 h to obtain enzymatic fermentation solution;

step 6, performing ultrafiltration by using an ultrafiltration membrane with a molecular weight-cut-off in a range of 1-10 kilodaltons (kD) on the enzymatic fermentation solution, and then performing nanofiltration by using a nanofiltration membrane with a molecular weight-cut-off in a range of 100-2,000 D, thereafter performing spray drying at an inlet temperature of 160° C.-220° C. and an outlet temperature of 90° C.-120° C. to obtain a finished product of a type III collagen peptide.

The *Cladosporium* used in the disclosure is purchased from Shanghai Baolu Biotechnology Co., Ltd; the *Candida famata* is self-separated from Hunan bacon, and is identified by phenotype and biochemical identification; the *Bacillus coagulans* is purchased from Shandong Zhongke Jiayi Biological Engineering Co. Ltd; and human type III collagen test kit is purchased from Shanghai Primary Biotechnology Co. Ltd.

In the disclosure, the pH values of the materials are adjusted by using an acidic pH regulator or an alkaline pH regulator. Among them, the acidic pH regulator is a mixture of one or more of citric acid, lactic acid, malic acid, hydrochloric acid, acetic acid, phosphoric acid, and tartaric acid; and the alkaline pH regulator is a soluble alkali, and is specifically a mixture of any one or more of NaOH, sodium carbonate ($Na_2CO_3$), sodium bicarbonate ($NaHCO_3$), potassium carbonate ($K_2CO_3$), potassium bicarbonate ($KHCO_3$), calcium carbonate ($CaCO_3$), and calcium oxide (CaO).

The disclosure will be further described below in a manner of illustrating embodiments. Various chemical reagents used in the embodiments of the disclosure are obtained by conventional commercial routes, unless specified specification.

Embodiment 1

A preparation method a type III collagen peptide, including the following steps:

step 1, immersing 1,000 g of a sheepskin in 10 kilograms (kg) of NaOH solution with a mass fraction of 0.5% for 12 h, washing the sheepskin to be neutral, then mixing the sheepskin with water according to a mass ratio of the sheepskin to the water of 1:10, performing ultrasonic treatment for 2 times at a power of 200 W and a wind speed of 150 m/s, each time of the ultrasonic treatment being performed for 60 min, taking out the sheepskin subjected to the ultrasonic treatment, then adding the sheepskin into water with a 10 times volume of the sheepskin to obtain feed liquid, and inoculating $2\times10^5$ CFU/g of *Cladosporium* and $3\times10^5$ CFU/g of *Candida famata* according to a weight of the feed liquid, and then performing a fermentation on the feed liquid added with the *Cladosporium* and the *Candida famata* at 30° C. for 8 hours to obtain a total crude protein extract;

step 2, adding the total crude protein extract to 10 kg of purified water to obtain a mixed solution, adjusting a pH value of the mixed solution to 2.5, heating the mixed solution to a temperature 60° C., and preserving the temperature and extracting the total crude protein extract for 4 h to prepare a crude collagen extract;

step 3, adjusting a pH value of the crude collagen extract to 2.5, uniformly mixing 1 g of soybean polysaccharide, 4 g of egg white, and 2 g of potato starch to obtain a clarificant, adding the clarificant to the crude collagen extract, stewing the crude collagen extract added with the clarificant for 4 h to remove impurities, and then obtaining a supernatant for later use;

step 4, adding *Bacillus coagulans* of 0.5% of a mass of the supernatant into the supernatant, adjusting a pH value of the supernatant added with the *Bacillus coagulans* to 7.5, and performing a fermentation on the supernatant added with the *Bacillus coagulans* at 50° C. for 3 h to obtain a type III collagen;

step 5, adjusting a pH value of the type III collagen to 7.5, adding 9 g of alkaline protease, 3 g of self-made ginger protease, and 3 g of self-made squid viscera protease to the type III collagen to perform an enzymolysis at 55° C. for 4 h to obtain an enzymatic hydrolysate, adjusting a pH value of the enzymatic hydrolysate to 7.5, and then inoculating $2\times10^8$ CFU/g of *Staphylococcus simulans* according to a weight of the enzymatic hydrolysate to perform a fermentation on the enzymatic hydrolysate added with the *Staphylococcus simulans* at 37° C. for 4 h to obtain enzymatic fermentation solution; and step 6, performing ultrafiltration on the enzymatic fermentation solution by using a polysulfone ultrafiltration membrane with a molecular weight-cut-off of 10 kD, and then performing nanofiltration by using a polyamide nanofiltration membrane with a molecular weight-cut-off of 100 D, thereafter, performing spray drying at an inlet temperature of 190° C. and an outlet temperature of 90° C. to obtain a finished product of the type III collagen peptide.

A mass spectrometry method is used to determine the finished product of the present embodiment, a liquid chromatography mass spectrometry (LC-MS) is composed of a Vanquish analytical purification LC system and an Orbitrap Exploris 480 mass spectrometry from Thermo Fisher Scientific™, and a result shows that the finished product contains a symbolic peptide fragment of type III collagen, and an average molecular weight thereof is 1,267 Daltons.

Embodiment 2

A preparation method a type III collagen peptide in the embodiment 2 differs from the embodiment 1 in that, in the step 5, the compound protease includes 7.5 g of alkaline protease, 4 g of self-made ginger protease, and 3 g of self-made squid viscera protease. The remaining steps are the same as those in the embodiment 1. The finished product obtained in the present embodiment is determined by the mass spectrometry method, and a result shows that the finished product contains a symbolic peptide fragment of type III collagen, and an average molecular weight thereof is 1,348 Daltons.

Embodiment 3

A preparation method a type III collagen peptide in the embodiment 3 differs from the embodiment 1 in that, in the step 5, the compound protease includes 12 g of alkaline protease, 3 g of self-made ginger protease, and 3 g of self-made squid viscera protease. The remaining steps are the same as those in the embodiment 1. The finished product obtained in the present embodiment is determined by the mass spectrometry method, and a result shows that the finished product contains a symbolic peptide fragment of type III collagen, and an average molecular weight thereof is 1,052 Daltons.

Embodiment 4

A preparation method a type III collagen peptide in the embodiment 4 differs from the embodiment 1 in that, in the step 5, the compound protease includes 3 g of alkaline protease, 3 g of self-made ginger protease, and 3 g of self-made squid viscera protease. The remaining steps are the same as those in the embodiment 1. The finished product obtained in the present embodiment is determined by the mass spectrometry method, and a result shows that the finished product contains a symbolic peptide fragment of type III collagen, and an average molecular weight thereof is 1,495 Daltons.

Comparative Example 1

A preparation method a type III collagen peptide in the comparative example 1 differs from the embodiment 1 in that, in the step 5, the compound protease includes 9 g of alkaline protease, 3 g of self-made ginger protease, and no squid viscera protease. The remaining steps are the same as those in the embodiment 1. The finished product obtained in the present embodiment is determined by the mass spectrometry method, and a result shows that the finished product does not contain a symbolic peptide fragment of type III collagen, and an average molecular weight thereof is 1,467 Daltons.

Comparative Example 2

A preparation method a type III collagen peptide in the comparative example 2 differs from the embodiment 1 in that, in the step 5, the compound protease includes 9 g of alkaline protease, 3 g of self-made squid viscera protease, and no self-made ginger protease. The remaining steps are the same as those in the embodiment 1. The finished product obtained in the present embodiment is determined by the mass spectrometry method, and a result shows that the finished product does not contain a symbolic peptide fragment of type III collagen, and an average molecular weight thereof is 1,726 Daltons.

Comparative Example 3

A preparation method a type III collagen peptide in the comparative example 3 differs from the embodiment 1 in that, in the step 5, the compound protease is replaced with 9 g of alkaline protease, which does not include a self-made squid viscera protease, nor a self-made ginger protease. The remaining steps are the same as those in the embodiment 1. The finished product obtained in the present embodiment is determined by the mass spectrometry method, and a result shows that the finished product does not contain a symbolic peptide fragment of type III collagen, and an average molecular weight thereof is 1,863 Daltons.

Comparative Example 4

A preparation method a type III collagen peptide, including the following steps:
step 1, immersing 1,000 g of a sheepskin in 10 kg of NaOH solution with a mass fraction of 0.5% for 12 h, washing the sheepskin to be neutral, then mixing the sheepskin with water according to a mass ratio of the sheepskin to the water of 1:10, performing ultrasonic treatment for 2 times at a power of 200 W and a wind speed of 150 m/s, each time of the ultrasonic treatment being performed for 60 min, taking out the sheepskin subjected to the ultrasonic treatment, then adding the sheepskin into water with a 10 times volume of the sheepskin to obtain feed liquid, and inoculating $2 \times 10^5$ CFU/g of *Cladosporium* and $3 \times 10^5$ CFU/g of *Candida famata* according to a weight of the feed liquid, and then performing a fermentation on the feed liquid added with the *Cladosporium* and the *Candida famata* at 30° C. for 8 h to obtain a total crude protein extract;
step 2, adding the total crude protein extract to 10 kg of purified water to obtain a mixed solution, adjusting a pH value of the mixed solution to 2.5, heating the mixed solution to a temperature 60° C., and preserving the temperature and extracting the total crude protein extract for 4 h to prepare a crude collagen extract;
step 3, adjusting a pH value of the crude collagen extract to 2.5, uniformly mixing 1 g of soybean polysaccharide, 4 g of egg white, and 2 g of potato starch to obtain a clarificant, adding the clarificant to the crude collagen extract, stewing the crude collagen extract added with the clarificant for 4 h to remove impurities, and then obtaining a supernatant for later use;
step 4, adjusting a pH value of the supernatant to 7.5, adding 9 g of alkaline protease, 3 g of self-made ginger protease, and 3 g of self-made squid viscera protease to the supernatant to perform an enzymolysis at 55° C. for 4 h to obtain an enzymatic hydrolysate, adjusting a pH value of the enzymatic hydrolysate to 7.5, and then inoculating $2 \times 10^8$ CFU/g of *Staphylococcus simulans* according to a weight of the enzymatic hydrolysate to perform a fermentation on the enzymatic hydrolysate added with the *Staphylococcus simulans* at 37° C. for 4 h to obtain enzymatic fermentation solution; and
step 5, performing ultrafiltration on the enzymatic fermentation solution by using a polysulfone ultrafiltration membrane with a molecular weight-cut-off of 10 kD, and then performing nanofiltration by using a polyamide nanofiltration membrane with a molecular weight-cut-off of 100 D, thereafter, performing spray drying at an inlet temperature of 190° C. and an outlet temperature of 90° C. to obtain a finished product of the type III collagen peptide.

The finished product obtained in the present comparative example is determined, and a result shows that the finished product does not contain a symbolic peptide fragment of type III collagen, and an average molecular weight thereof is 2,425 Daltons.

Comparative Example 5

A preparation method a type III collagen peptide, including the following steps:
step 1, immersing 1,000 g of a sheepskin in 10 kg of NaOH solution with a mass fraction of 0.5% for 12 h, washing the sheepskin to be neutral, then mixing the sheepskin with water according to a mass ratio of the sheepskin to the water of 1:10, performing ultrasonic treatment for 2 times at a power of 200 W and a wind speed of 150 m/s, each time of the ultrasonic treatment being performed for 60 min, taking out the sheepskin subjected to the ultrasonic treatment, then adding the sheepskin into water with a 10 times volume of the sheepskin to obtain feed liquid, and inoculating $2 \times 10^5$ CFU/g of *Cladosporium* and $3 \times 10^5$ CFU/g of *Candida famata* according to a weight of the feed liquid, and then performing a fermentation on the feed liquid added with the *Cladosporium* and the *Candida famata* at 30° C. for 8 h to obtain a total crude protein extract;
step 2, adding the total crude protein extract to 10 kg of purified water to obtain a mixed solution, adjusting a pH value of the mixed solution to 2.5, heating the mixed solution to a temperature 60° C., and preserving the temperature and extracting the total crude protein extract for 4 h to prepare a crude collagen extract;
step 3, adjusting a pH value of the crude collagen extract to 2.5, uniformly mixing 1 g of soybean polysaccharide, 4 g of egg white, and 2 g of potato starch to obtain a clarificant, adding the clarificant to the crude collagen extract, stewing the crude collagen extract added with the clarificant for 4 h to remove impurities, and then obtaining a supernatant for later use;
step 4, adding *Bacillus coagulans* of 0.5% of a mass of the supernatant into the supernatant, adjusting a pH value of the supernatant added with the *Bacillus coagulans* to 7.5, and performing a fermentation on the supernatant added with the *Bacillus coagulans* at 50° C. for 3 h to obtain a type III collagen;
step 5, adjusting a pH value of the type III collagen to 7.5, adding 9 g of alkaline protease, 3 g of self-made ginger protease, and 3 g of self-made squid viscera protease to the type III collagen to perform an enzymolysis at 55° C. for 4 h to obtain an enzymatic hydrolysate; and step 6, performing ultrafiltration on the enzymatic hydrolysate by using a polysulfone ultrafiltration membrane with a molecular weight-cut-off of 10 kD, and then performing nanofiltration by using a polyamide nanofiltration membrane with a molecular weight-cut-off of 100 D, thereafter, performing spray drying at an inlet temperature of 190° C. and an outlet temperature of 90° C. to obtain a finished product of the type III collagen peptide.

The finished product obtained in the present comparative example is determined, and a result shows that the finished product does not contain a symbolic peptide fragment of type III collagen, and an average molecular weight thereof is 2,298 Daltons.

Comparative Example 6

A preparation method a type III collagen peptide, including the following steps:
step 1, immersing 1,000 g of a sheepskin in 10 kg of NaOH solution with a mass fraction of 0.5% for 12 h, washing the sheepskin to be neutral, then mixing the sheepskin with water according to a mass ratio of the sheepskin to the water of 1:10, performing ultrasonic treatment for 2 times at a power of 200 W and a wind speed of 150 m/s, each time of the ultrasonic treatment being performed for 60 min, taking out the sheepskin subjected to the ultrasonic treatment, then adding the sheepskin into water with a 10 times volume of the sheepskin to obtain feed liquid, and inoculating $2\times10^5$ CFU/g of *Cladosporium* and $3\times10^5$ CFU/g of *Candida famata* according to a weight of the feed liquid, and then performing a fermentation on the feed liquid added with the *Cladosporium* and the *Candida famata* at 30° C. for 8 h to obtain a total crude protein extract;

step 2, adding the total crude protein extract to 10 kg of purified water to obtain a mixed solution, adjusting a pH value of the mixed solution to 2.5, heating the mixed solution to a temperature 60° C., and preserving the temperature and extracting the total crude protein extract for 4 h to prepare a crude collagen extract;

step 3, adjusting a pH value of the crude collagen extract to 2.5, uniformly mixing 1 g of soybean polysaccharide, 4 g of egg white, and 2 g of potato starch to obtain a clarificant, adding the clarificant to the crude collagen extract, stewing the crude collagen extract added with the clarificant for 4 h to remove impurities, and then obtaining a supernatant for later use;

step 4, adjusting a pH value of the supernatant to 7.5, adding 9 g of alkaline protease to the supernatant to perform an enzymolysis at 55° C. for 4 h to obtain an enzymatic hydrolysate; and step 5, performing ultrafiltration on the enzymatic hydrolysate by using a polysulfone ultrafiltration membrane with a molecular weight-cut-off of 10 kD, and then performing nanofiltration by using a polyamide nanofiltration membrane with a molecular weight-cut-off of 100 D, thereafter, performing spray drying at an inlet temperature of 190° C. and an outlet temperature of 90° C. to obtain a finished product of the type III collagen peptide.

The finished product obtained in the present comparative example is determined, and a result shows that the finished product does not contain a symbolic peptide fragment of type III collagen, and an average molecular weight thereof is 2,761 Daltons.

RESULTS

The collagen peptides prepared by the methods described above in the embodiments 1-4 contain the symbolic peptide fragment of type III collagen, and the collagen peptides prepared in the comparative examples 1-6 do not contain the symbolic peptide fragment of type III collagen. Therefore, it can be seen therefrom that processes of *Bacillus coagulans* fermentation, compound protease enzymolysis, and *Staphylococcus simulans* fermentation can affect the extraction of type III collagen, and each process within the three processes cooperates with and is combined with each other to effectively extract the type III collagen.

The finished products obtained in the above embodiments and comparative examples are taken as samples, and the samples are performed experiments to determine an influence of the samples on human fibroblasts to secrete the type III collagen. An experiment method is as follows.

Human skin fibroblasts (HSF) in logarithmic growth period are digested with 0.25% pancreatin, and then laid into a 12-well plate, and cultured overnight until a cell convergence rate is 80-90%. The type III collagen peptides obtained in the embodiments 1-4 and the comparative examples 1-6 of the disclosure are diluted to 100 milligrams per liter (mg/L), respectively, to obtain corresponding dilute solution, and then supernatants of the HSF are added into the dilute solution, respectively. Specially, a blank group is obtained by adding the supernatant of the HSF into normal saline. Thereafter, 10 groups of the dilute solution added with the HSF and the blank group are gently mixed for continue cultivation for 3 days to obtain corresponding cultures, then the cultures are centrifuged to obtain corresponding supernatants, and then the supernatants are taken to determine by using human type III collagen test kits, respectively.

The experimental results are illustrated in Table 1 below.

TABLE 1

| Group | Concentration of type III collagen (pg/mL) |
| --- | --- |
| Blank group | 12.46 ± 2.51 |
| Embodiment 1 | 43.51** ± 4.86 |
| Embodiment 2 | 38.22** ± 3.53 |
| Embodiment 3 | 39.69** ± 2.57 |
| Embodiment 4 | 36.42** ± 3.18 |
| Comparative example 1 | 16.44 ± 1.87 |
| Comparative example 2 | 17.05 ± 2.48 |
| Comparative example 3 | 15.96 ± 2.13 |
| Comparative example 4 | 17.79 ± 3.61 |
| Comparative example 5 | 14.93 ± 2.83 |
| Comparative example 6 | 17.28 ± 2.09 |

Note:
**illustrated in the Table 1 means that the result is compared to that of the blank group and p is less than 0.01.

It can be seen from the experimental results that the type III collagen peptides obtained in the embodiments 1-4 can specifically promote the generation of the type III collagen, which have significant differences from the blank group; and the comparative examples 1-6 have no significant differences compared to the blank group. Therefore, the disclosure can prepare the type III collagen peptide through mutual coordination of the processes of *Bacillus coagulans* fermentation, compound protease enzymolysis, and *Staphylococcus simulans* fermentation, and the prepared type III collagen peptide can promote the generation of the type III collagen in human's body.

The above content is merely an example and an illustration of the concept of the disclosure, and those skilled in the related art would have been able to make various modifications or additions to the described embodiments or replace the described embodiments in a similar manner. However, if the modifications or additions or replacements do not depart from the concept of the disclosure or beyond the scope defined by the specification of the disclosure, they should fall within the scope of the protection of the disclosure.

What is claimed is:

1. A preparation method for obtaining a type III collagen peptide, comprising:
    step 1, degreasing a raw material to obtain a degreased raw material, performing ultrasonic treatment and fermentation on the degreased raw material to obtain a total crude protein extract;
    step 2, extracting a crude collagen extract from the total crude protein extract under an acidic condition;
    step 3, adding a clarificant to remove impurities in the crude collagen extract and obtaining a supernatant thereof;
    step 4, adding *Bacillus coagulans* to the supernatant for fermentation to obtain a type III collagen;
    step 5, adding a compound protease to the type III collagen for enzymolysis, followed by inoculating with *Staphylococcus simulans* for fermentation to obtain an enzymatic fermentation solution; and
    step 6, separating and purifying the enzymatic fermentation solution to obtain the type III collagen peptide;

wherein the compound protease comprises: an alkaline protease and a self-made protease, and the self-made protease comprises: a ginger protease and a squid viscera protease;

wherein a mass ratio of the alkaline protease:the ginger protease:the squid viscera protease is in a range of 2.5-4:0.8-1.5:1;

wherein the step 1 further comprises the following steps: immersing the raw material in a sodium hydroxide (NaOH) solution, taking out and washing the raw material to be a neutral pH, then mixing the raw material with water according to a mass ratio of the raw material to the water of 1:5-40, performing the ultrasonic treatment for 1-3 times, taking out the raw material after performing the ultrasonic treatment, then adding the raw material into water with a 1-10 times volume of the raw material again to obtain feed liquid, and inoculating *Cladosporium* and/or *Candida famata* for the fermentation according to a weight of the feed liquid, thereby obtaining the total crude protein extract; and wherein the raw material is one selected from the group consisting of a tilapia, a cod, a sheepskin, a cowhide, and a poultry skin.

2. The preparation method according to claim 1, wherein an inoculation amount of the *Cladosporium* is in a range of $1-8\times10^5$ colony-forming units per gram (CFU/g), and an inoculation amount of the *Candida famata* is in a range of $1-8\times10^5$ CFU/g.

3. The preparation method according to claim 1, wherein the step 2 further comprises the following steps:

adding the total crude protein extract to purified water with a 2-50 times mass of the total crude protein extract, adjusting a potential of hydrogen (pH) value of the total crude protein extract to a range of 2-5, heating the total crude protein extract added with the purified water to a temperature of 50-90 degrees Celsius (° C.), and preserving the temperature and extracting the total crude protein extract for 2-8 hours (h) to prepare the crude collagen extract.

4. The preparation method according to claim 1, wherein the step 3 further comprises the following steps:

adjusting a pH value of the crude collagen extract to a range of 2-7, adding the clarificant to the crude collagen extract, stewing the crude collagen extract added with the clarificant for 2-8 h to remove the impurities, and then obtaining the supernatant for later use.

5. The preparation method according to claim 4, wherein the clarificant is a mixture of soybean polysaccharide, egg white and potato starch, and a mixing mass ratio of the soybean polysaccharide:the egg white:the potato starch is in a range of 1:2-4:1-3; and an addition amount of the clarificant is in a range of 0.5%-3% of a mass of the crude collagen extract.

6. The preparation method according to claim 1, wherein the step 4 further comprises the following steps:

adding the *Bacillus coagulans* to the supernatant obtained in the step 3, adjusting a pH value of the supernatant added with the *Bacillus coagulans* to a range of 6-7.5, and performing the fermentation on the supernatant added with the *Bacillus coagulans* at 40° C.-55° C. for 2-6 h to obtain the type III collagen.

7. The preparation method according to claim 6, wherein an addition amount of the *Bacillus coagulans* is in a range of 0.1%-1% of a mass of the supernatant.

8. The preparation method according to claim 1, wherein the step 5 further comprises the following steps:

adjusting a pH value of the type III collagen to a range of 7.5-8.0, adding the compound protease to the type III collagen to perform the enzymolysis to obtain an enzymatic hydrolysate; adjusting a pH value of the enzymatic hydrolysate to a range of 6-7.5, and then inoculating the *Staphylococcus simulans* to perform the fermentation on the enzymatic hydrolysate added with the *Staphylococcus simulans*, thereby obtaining the enzymatic fermentation solution.

9. The preparation method according to claim 8, wherein an addition amount of the compound protease is in a range of 0.5%-2% of a mass of the type III collagen.

10. The preparation method according to claim 1, wherein the *Staphylococcus simulans* is self separated obtained from Hunan bacon, and is identified by phenotype and biochemical identification; and an inoculation amount of the *Staphylococcus simulans* is in a range of $1-9\times10^8$ CFU/g.

11. The preparation method according to claim 1, wherein steps of the separating and purifying comprise: ultrafiltration, nanofiltration, and spray drying.

12. The preparation method according to claim 11, wherein a molecular weight-cut-off of an ultrafiltration membrane used in the ultrafiltration is in a range of 1-10 kilodaltons (kD), and the ultrafiltration membrane is a polysulfone or a polyamide spiral-wound membrane; and a molecular weight-cut-off of a nanofiltration membrane used in the nanofiltration is in a range of 100-2,000 D, and the nanofiltration membrane is one selected from the group consisting of a polyamide, a sulfonated polyethersulfone, and a sulfonated polysulfone hollow fiber membrane.

\* \* \* \* \*